(12) United States Patent
Kawasaki et al.

(10) Patent No.: US 12,194,184 B2
(45) Date of Patent: Jan. 14, 2025

(54) DECONTAMINATION DEVICE AND PASS BOX IN WHICH SAME IS DISPOSED

(71) Applicant: AIREX CO., LTD., Aichi (JP)

(72) Inventors: Koji Kawasaki, Aichi (JP); Daisuke Kakuda, Aichi (JP); Jun Masudome, Aichi (JP); Haruka Futamura, Aichi (JP); Yukihiro Yazaki, Aichi (JP); Tsukasa Kitano, Aichi (JP); Zhiqiang Guo, Aichi (JP); Ayumi Ogawa, Aichi (JP)

(73) Assignee: AIREX CO., LTD. (JP)

( * ) Notice: Subject to any disclaimer, the term of this patent is extended or adjusted under 35 U.S.C. 154(b) by 778 days.

(21) Appl. No.: 17/442,319

(22) PCT Filed: Mar. 16, 2020

(86) PCT No.: PCT/JP2020/011481
§ 371 (c)(1),
(2) Date: Feb. 15, 2022

(87) PCT Pub. No.: WO2020/196036
PCT Pub. Date: Oct. 1, 2020

(65) Prior Publication Data
US 2022/0184259 A1    Jun. 16, 2022

(30) Foreign Application Priority Data
Mar. 28, 2019 (JP) ................. 2019-062731

(51) Int. Cl.
*A61L 2/22* (2006.01)
*A61L 2/025* (2006.01)

(52) U.S. Cl.
CPC ............. *A61L 2/22* (2013.01); *A61L 2/025* (2013.01); *A61L 2202/122* (2013.01); *A61L 2202/14* (2013.01)

(58) Field of Classification Search
CPC ... A61L 2/22; A61L 2/26; A61L 2/025; A61L 2202/14; A61L 2202/122; A61L 2202/23
See application file for complete search history.

(56) References Cited

U.S. PATENT DOCUMENTS

2005/0042130 A1* 2/2005 Lin ................... A61L 2/208
422/33
2018/0360077 A1 12/2018 Krebs et al.

FOREIGN PATENT DOCUMENTS

| JP | H01178041 U | 12/1989 |
|---|---|---|
| JP | 2004537345 A | 12/2004 |
| JP | 2006198120 A | 8/2006 |

OTHER PUBLICATIONS

PCT International Search Report, PCT/JP2020/011481, Jun. 2, 2020, 5 pages.

* cited by examiner

*Primary Examiner* — Lessanework Seifu
(74) *Attorney, Agent, or Firm* — Quarles & Brady LLP; Yakov Sidorin

(57) ABSTRACT

A decontamination device devised to accomplish decontamination with a proper amount of decontamination agent by employing a mist control mechanism to concentrate a mist for decontamination on the surface of an article to be conveyed, and to reduce duration of operations such as aeration increase efficiency of decontamination, and a pass box in which the decontamination device is disposed. The device also includes a mist supply means configured to convert a chemical for decontamination into the mist, and to supply the mist to the inside of a working chamber accommodating the article. The mist control mechanism includes vibration boards adjacent to internal wall surfaces of the working chamber, which are ultrasonically vibrated to generate sound flows from board surfaces by an ultrasound in (Continued)

the vertical direction. The mist supplied to the inside of the chamber is pressed by acoustic radiation pressure to be concentrated on external surfaces of the article

DECONTAMINATION DEVICE AND PASS BOX IN WHICH SAME IS DISPOSED

CROSS-REFERENCE TO RELATED APPLICATIONS

This application represents the US national stage entry from the International Application No. PCT/JP2020/011481, filed on 16 Mar. 2020, that claims priority from the Japanese Patent Application No. JP 2019-062731 filed on Mar. 28, 2019. The disclosure of each of the above-identified patent documents is incorporated by reference herein.

TECHNICAL FIELD

The present invention relates to a decontamination device for efficiently decontaminating an isolator and an associated article thereof in a pass box and, more particularly, to a decontamination device including a mist control mechanism. Also, the present invention relates to a pass box in which a decontamination device including a mist control mechanism is disposed.

BACKGROUND ART

In manufacturing settings for pharmaceutical or food products or in the clinical environment such as operating rooms, the indoor working area must inevitably be kept sterile. Particularly in cases where clean rooms as a working chamber for manufacturing pharmaceutical products are decontaminated, advanced decontamination validation needs to be accomplished in accordance with Good Manufacturing Practice (GMP).

In a small-scale work in such a clean environment, a small chamber is employed as a working chamber, and an isolator is used for an operator to work through a glove or a half-suit from the outside of the chamber. The isolator chamber is provided with an intake and exhaust device for maintaining a sterile state so as to receive no contaminants from the external environment. In addition, a sterile state is intended to be maintained when necessary equipment and articles are conveyed to the inside of an isolator in the sterile state from the external environment.

For example, a small spare chamber for conveying, called as a "pass box", is provided for an article to be conveyed to the inside of the isolator. An operator, when conveying an article to the inside of the isolator, first conveys the article to a pass box. In this case, a carry-in door between the isolator and the pass box is sealed. Subsequently, the carry-in door between the pass box and the external environment is sealed to decontaminate the article together with the inside of the pass box. After the pass box is completely decontaminated and a gas for decontamination or the like is removed, the carry-in door between the isolator and the pass box is opened to convey the article to the inside of the isolator.

In recent years, hydrogen peroxide has widely been used (in the form of a gas or mist) to decontaminate a working chamber such as an isolator and a pass box (hereinafter referred to as a "room to be decontaminated") and articles to be conveyed. Advantageously, hydrogen peroxide has a strong sterilization effect, and is inexpensively available and effectively utilized as an environmentally-friendly decontamination gas that is ultimately decomposed into oxygen and water.

The following patent document 1 describes that the decontamination effect by hydrogen peroxide is provided by a condensed film of a hydrogen peroxide solution that condenses on the surface of an object to be decontaminated. Accordingly, in order to accomplish the decontamination effect in a room to be decontaminated, hydrogen peroxide may be supplied in large quantities to make thick or in a higher concentration the resulting condensed film composed of a hydrogen peroxide solution.

CITATION LIST

Patent Literature

Patent Document 1: JP-A-61-004543

SUMMARY OF THE INVENTION

Technical Problem

In fact, the supply of an excessive amount of hydrogen peroxide to a room to be decontaminated causes extreme condensation, and the resulting condensed film from a high concentration of hydrogen peroxide solution disadvantageously corrodes wall surfaces and other portions of a room to be contaminated. After a decontamination work using hydrogen peroxide, aeration is performed with clean air to remove the residual hydrogen peroxide and condensed film inside the room to be decontaminated. However, the supply of such an excessive amount of hydrogen peroxide is problematic due to longer duration required in the aeration operation for removing a high concentration of condensed film of a hydrogen peroxide solution generated on wall surfaces and other portions of the room to be decontaminated. In addition, a complicated shape of an article to be conveyed into an isolator unfortunately brings about much more time for aeration.

Also, decontamination of the article within the pass box is the major operation for the article to be conveyed to the isolator through the pass box. Internal wall surfaces of the pass box are already decontaminated prior to conveying of the article. Therefore, the input of a decontamination agent such as hydrogen peroxide is preferably concentrated on the surface of the conveyed article, and the decontamination efficiency improves by avoiding condensation of an excessive amount of decontamination agent on the internal wall surfaces of the pass box.

Thus, the present invention was made in view of the situation to solve the problems, and has an object to provide a decontamination device capable of accomplishing a decontamination effect with a proper amount of decontamination agent by employing a mist control mechanism and concentrating a mist for decontamination on the surface of an article to be conveyed, and reducing the duration of operations such as aeration to achieve more efficient decontamination works, and a pass box in which same is disposed.

Solution to the Problem

To solve the aforementioned problem, inventors of the present invention have carried out an extended investigation to find that a proper condensed film can be formed by employing ultrasonic vibration in a mist control mechanism, refining a mist of a hydrogen peroxide solution supplied to a room to be decontaminated, and concentrating the mist of a hydrogen peroxide solution on the surface of the article in the room to be decontaminated. Based on that technique, the present invention was accomplished.

Specifically, a decontamination device according to the present invention is, according to description in claim 1, a decontamination device (20, 120) for decontaminating an article (50, 150) accommodated inside a working chamber (10, 110), the decontamination device including a mist supply means (30, 130) and a mist control means (40, 140), characterized in that the mist supply means converts a chemical for decontamination into a mist for decontamination, and supplies the same to the inside of the working chamber that accommodates the article, the mist control mechanism includes vibration boards (41, 42, 43, 44, 141, 142) disposed adjacent to internal wall surfaces of the working chamber, and the vibration boards are subjected to ultrasonic vibration to generate sound flows (41$b$, 42$b$, 43$b$, 44$b$, 141$b$, 142$b$) from board surfaces (41$a$, 42$a$, 43$a$, 44$a$, 141$a$, 142$a$) by an ultrasound in the vertical direction, and the mist for decontamination supplied to the working chamber is pressed by acoustic radiation pressure to concentrate the mist for decontamination on external surfaces of the article.

Moreover, the present invention is, according to description in claim 2, the decontamination device according to claim 1, characterized in that the mist control mechanism includes a plurality of vibration boards, the plurality of vibration boards is arranged with the article placed therebetween and board surfaces thereof being opposite each other, and the resulting pressing force by the acoustic radiation pressure primarily concentrates in the direction of the article from each of the vibration boards, and the mist for decontamination is controlled to concentrate on external surfaces of the article.

Furthermore, the present invention is, according to description in claim 3, the decontamination device according to claim 1, characterized in that the mist control mechanism includes a plurality of vibration boards, the plurality of vibration boards is arranged with the article placed therebetween and without board surfaces thereof being opposite each other, and the resulting pressing force by the acoustic radiation pressure primarily passes along a side surface of the article from each of the vibration boards, and the mist for decontamination is controlled to concentrate on external surfaces of the article by moving so as to rotate inside the working chamber.

Moreover, the present invention is, according to description in claim 4, the decontamination device according to any one of claims 1 to 3, characterized in that the vibration board includes a base and a plurality of transmitters, the plurality of transmitters is arranged on a planar surface of the base so as to be uniform in transmission directions, and the transmitters are operated in the same phase, whereby a sound flow is generated by a significantly directional ultrasound from the board surface of the vibration board in the vertical direction by mutually amplifying the ultrasounds of the plurality of transmitters in the front direction (which is substantially perpendicular to the board surface) and mutually canceling out the ultrasounds of the plurality of transmitters in a lateral direction (that is transverse to the front direction).

Furthermore, the present invention is, according to description in claim 5, the decontamination device according to any one of claims 1 to 4, characterized in that the mist for decontamination supplied to the inside of the working chamber is further miniaturized or reduced in size by ultrasonic vibration generated from the vibration board.

Moreover, the present invention is, according to description in claim 6, the decontamination device according to any one of claims 1 to 5, characterized in that the decontamination device includes a control means for changing the frequency and output of the ultrasound generated from the vibration board and/or for transmitting an ultrasound intermittently to control the position or moving speed of the mist for decontamination controlled to concentrate on external surfaces of the article.

Furthermore, a pass box according to the present invention, according to description in claim 7, includes therein the decontamination device according to any one of claims 1 to 6.

Advantageous Effects of Invention

According to the above configuration, the decontamination device of the present invention includes a mist supply means and a mist control means. The mist supply means converts a chemical for decontamination into a mist for decontamination, and supplies the same to the inside of a working chamber that accommodates the article. The mist control mechanism includes vibration boards disposed adjacent to internal wall surfaces of the working chamber, and the vibration boards are subjected to ultrasonic vibration to generate sound flows from board surfaces by an ultrasound in the vertical direction. Accordingly, the mist for decontamination supplied to the working chamber is pressed by acoustic radiation pressure to concentrate the mist for decontamination on external surfaces of the article.

Accordingly, it is possible to provide a decontamination device capable of accomplishing a decontamination effect with a proper amount of decontamination agent by employing a mist control mechanism and concentrating a mist for decontamination on the surface of an article to be conveyed, and reducing the duration of operations such as aeration to achieve more efficient decontamination works.

According to the above configuration, the mist control mechanism may include a plurality of vibration boards. The plurality of vibration boards is arranged with the article placed therebetween and board surfaces thereof being opposite each other, and the resulting pressing force by the acoustic radiation pressure primarily concentrates in the direction of the article from each of the vibration boards. Accordingly, the mist for decontamination is controlled to concentrate on external surfaces of the article. Thus, the above operational advantage can more specifically be provided.

According to the above configuration, the mist control mechanism may include a plurality of vibration boards. The plurality of vibration boards is arranged with the article placed therebetween and without board surfaces thereof being opposite each other, and the resulting pressing force by the acoustic radiation pressure primarily passes along a side surface of the article from each of the vibration boards. Accordingly, the mist for decontamination concentrates on external surfaces of the article by moving so as to rotate inside the working chamber. Thus, the above operational advantage can more specifically be provided.

According to the above configuration, the vibration board includes a base and a plurality of transmitters, and the plurality of transmitters is arranged on a plane or planar surface of the base so as to be uniform in transmission directions, and the transmitters are operated in the same phase. Consequently, the ultrasounds of the plurality of transmitters in the front direction are mutually amplified, and the ultrasounds of the plurality of transmitters in the lateral direction are mutually canceled out. Accordingly, a sound flow can be generated by a significantly directional ultrasound from the board surface of the vibration board in the vertical direction. Thus, the above operational advantage can more specifically be provided.

According to the above configuration, the mist for decontamination supplied to the inside of the working chamber is further miniaturized by ultrasonic vibration generated from the vibration board. Accordingly, the above operational advantage can more specifically be provided.

According to the above configuration, the decontamination device may include a control means for changing the frequency and output of the ultrasound generated from the vibration board. The decontamination device may include a control means for transmitting an ultrasound intermittently. Accordingly, the position or moving speed of the mist for decontamination controlled to concentrate on external surfaces of the article can be controlled. Thus, the above operational advantage can more specifically be provided.

According to the above configuration, the pass box according to the present invention includes therein the decontamination device according to any one of claims 1 to 7.

Accordingly, it is possible to provide a decontamination device capable of accomplishing a decontamination effect with a proper amount of decontamination agent by disposing a decontamination device including a mist control mechanism and concentrating a mist for decontamination on the surface of an article to be conveyed, and reducing the duration of operations such as aeration to achieve more efficient decontamination works.

DETAILED DESCRIPTION

In the present invention, "mist" is broadly interpreted and defined as the state of a liquid droplet of a decontamination agent miniaturized and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the mist according to the present invention is categorized into a "mist" (the size may be defined as 10 μm or less) or a "fog" (the size may be defined as 5 μm or less), and a mist having a larger particle size. In the present invention, ultrasonic vibration converts even a mist, a fog and a liquid droplet sized 3 to 10 μm into equalized ultrafine particles 3 μm or less to provide high-level decontamination effects (later described).

The decontamination device according to the present invention and a pass box in which same is disposed will be described with reference to each embodiment. The present invention is not restricted to each of the following embodiments.

First Embodiment

Figures 1A, 1B:
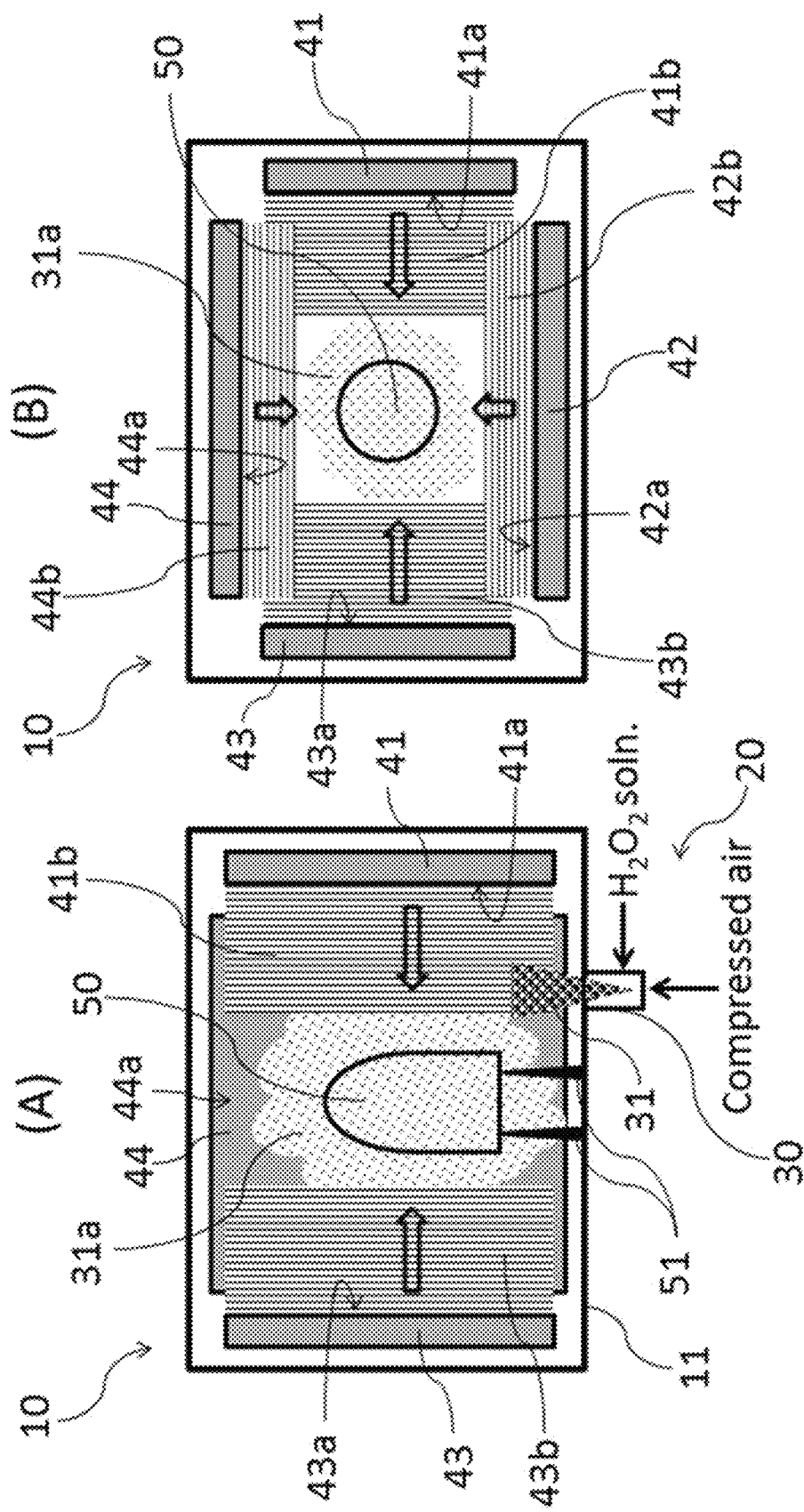
FIG. 1A is a schematic front cross-sectional view and FIG. 1B is a schematic plane cross-sectional view, each showing the inside of a pass box including a decontamination device according to a first embodiment.

A first embodiment will be described with reference to a decontamination device included in a pass box. FIG. 1(A) is a schematic front cross-sectional view and FIG. 1(B) is a schematic plane cross-sectional view, each showing the inside of a pass box including a decontamination device according to the first embodiment.

In FIGS. 1A, 1B, a pass box 10 is a stainless housing that is linked to an isolator (not shown) through an opening/closing door (inner door) on a wall surface thereof, the isolator including an opening/closing door (outer door) on other wall surface, leading to the external environment. The linking state between the pass box 10 and the isolator and the structure of opening/closing doors are not particularly restricted, and the pass box is the same as conventional pass boxes in structure. The position of the pass box relative to the isolator is not restricted to that on a side wall surface, and the pass box may be linked to a top wall surface or a bottom wall surface. The inside of the pass box may include an air supply and exhaust device for decontamination and aeration. FIGS. 1A, 1B shows no inner door, outer door, air supply and exhaust device, or the like.

In FIGS. 1A, 1B, an article 50 that is conveyed from the external environment to the inside of the isolator is conveyed to a center inside the pass box 10. In this first embodiment, the article 50 is to be decontaminated and is conveyed to the inside of the isolator after it is decontaminated by a decontamination device 20 in the pass box. In FIG. 1A, the article 50 is supported by a deck 51 such that its bottom surface is readily decontaminated. In fact, the deck 51 is not always necessary, and a decontamination mist may be allowed to enter the bottom surface, depending on the shape of the bottom surface of the article 50, or by achieving resonance of the article 50 by ultrasonic vibration.

In FIGS. 1A, 1B, the pass box 10 includes therein the decontamination device 20. The decontamination device 20 is composed of a mist supply unit 30, a mist control unit 40, and an ultrasonic controller (not shown). In this first embodiment, the mist supply unit 30 used is a two-fluid spray nozzle 30 placed on a bottom wall surface of the pass box 10 (see FIG. 1A). In this first embodiment, the decontamination agent used is a hydrogen peroxide solution ($H_2O_2$ solution).

The two-fluid spray nozzle 30 converts a hydrogen peroxide solution into a hydrogen peroxide solution mist 31 by compressed air from a compressor (not shown) to supply the same to the inside of the pass box 10. In the present invention, the mist supply unit is not restricted to a two-fluid spray nozzle, and a mist generation mechanism and output are not particularly restricted.

Herein, a mist controller 40 will be described. In this first embodiment, the mist control unit 40 includes 4 vibration boards 41, 42, 43, 44. The 4 vibration boards 41, 42, 43, 44 are disposed inside 4 side walls of the pass box 10 against side wall surfaces such that vibration surfaces 41*a*, 42*a*, 43*a*, 44*a* face horizontally inside the pass box 10. These 4 vibration boards 41, 42, 43, 44 are arranged by allowing 2 board surfaces (vibration surfaces) thereof to be opposite each other (the board surfaces to face each other in front). Specifically, the vibration board 41 and the vibration board 43, and the vibration board 42 and the vibration board 43 are arranged by allowing their respective vibration surfaces to be opposite (see FIG. 1B). The reason for arranging these vibration boards by allowing them to be opposite each other and the action of the hydrogen peroxide solution mist 31 will be described later.

Figure 2:
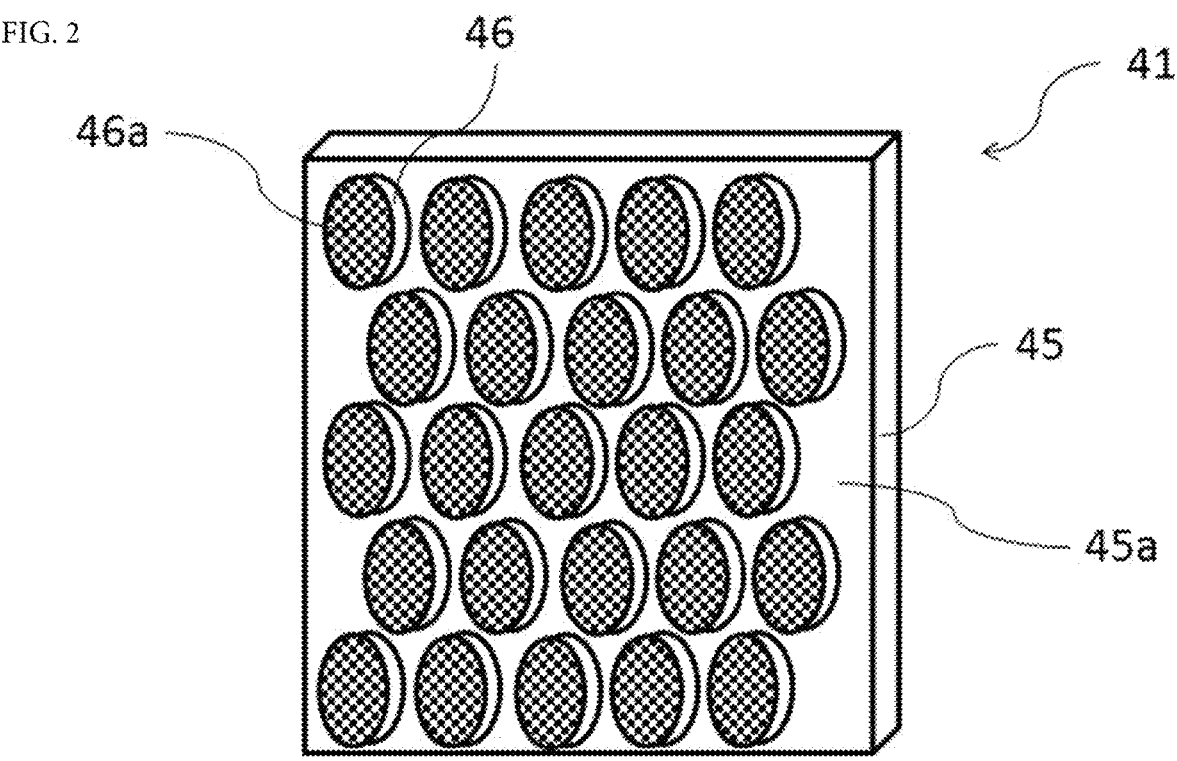
FIG. 2 is a schematic perspective view showing a plurality of ultrasonic speakers arranged in a speaker base in a vibration board included in the decontamination device in FIG. 1.

Herein, the vibration board 41 will be described (also applied to the vibration boards 42, 43, 44). FIG. 2 is a schematic perspective view showing a plurality of ultrasonic speakers arranged in a speaker base in a vibration board included in the decontamination device in FIG. 1. In FIG. 2, the vibration board 41 includes a base and a plurality of transmitters. In this first embodiment, the base used is a speaker base 45, and the transmitter used is an ultrasonic speaker 46. In this first embodiment, 25 ultrasonic speakers 46 are arranged on a plane or planar surface 45*a* of the speaker base 45 so as to be uniform in transmission direction of a vibration surface 46*a* (leftward as seen from the front shown). The number of ultrasonic speakers is not particularly restricted.

In this first embodiment, the ultrasonic speaker 46 used is an ultra directional ultrasonic speaker. Specifically, an ultrasonic speakers (DC12V, 50 mA) of frequency modulation system for transmitting an ultrasound whose frequency is around 40 KHz is used. The type, size, structure and output of the ultrasonic speaker are not particularly restricted. In the present invention, the vibration board included in the mist control device is not restricted to an ultrasonic speaker, and the ultrasonic generation mechanism, frequency range and output are not particularly restricted.

In this first embodiment, a plurality of (25) ultrasonic speakers 46 are arranged so as to be uniform in transmission direction the vibration surface 46*a*, and the transmitters are operated in the same phase to mutually amplify ultrasounds from the plurality of ultrasonic speakers 46 in the front direction and mutually cancel out ultrasounds from the plurality of ultrasonic speakers 46 in the lateral direction. Consequently, the ultrasonic speakers 46 arranged on the speaker base 45 are subjected to ultrasonic vibration to generate a significantly directional sound flow traveling in the air from each of the vibration surfaces 46*a* in the vertical direction. The frequency and output of the ultrasonic speakers 46 are controlled by an ultrasonic controller (not shown) to achieve efficient decontamination operations.

Subsequently, the action of the hydrogen peroxide solution mist 31 inside the pass box 10 including the decontamination device 20 according to the above configuration will be described. In FIG. 1, the vibration boards 41, 42, 43, 44 placed at 4 side walls inside the pass box 10 allow vibration surfaces 41*a*, 42*a*, 43*a*, 44*a* thereof to face the central portion of the pass box 10 (in the same direction as the direction of the vibration surface 46*a* of the ultrasonic speaker 46).

Ultrasonic vibration of the ultrasonic speaker of each vibration board in this state generates significantly directional sound flows 41*b*, 42*b*, 43*b*, 44*b* traveling in the vertical direction from the 4 vibration surfaces 41*a*, 42*a*, 43*a*, 44*a*, respectively. These sound flows 41*b*, 42*b*, 43*b*, 44*b* take in the hydrogen peroxide solution mist 31 discharged from the two-fluid spray nozzle 30, generate a pressing force by acoustic radiation pressure and move the hydrogen peroxide solution mist 31 to the central portion of the pass box 10. In this case, the hydrogen peroxide solution mist 31 is converted into a fine mist 31*a* miniaturized by the ultrasonic vibration from the sound flows 41*b*, 42*b*, 43*b*, 44*b*.

In FIGS. 1A, 1B, the 2 vibration boards 41, 43 are arranged with the article 50 interposed therebetween such that their vibration surfaces 41*a*, 43*a* are opposite. On the other hand, the other 2 vibration boards 42, 44 are arranged with the article 50 interposed therebetween such that their vibration surfaces 42*a*, 44*a* are opposite and form a substantially right angle with the vibration surfaces 41*a*, 43*a* of the vibration boards 41, 43.

In this state, the article 50 conveyed to the central portion of the pass box 10 is surrounded by the 4 vibration surfaces 41*a*, 42*a*, 43*a*, 44*a* of the 4 vibration boards 41, 42, 43, 44. Inventors of the present invention found that in this state the fine mist 31*a* miniaturized by ultrasonic vibration from the sound flows 41*b*, 42*b*, 43*b*, 44*b* concentrates in 4 directions on external surfaces of the article 50 located at the central portion of the pass box 10 (see FIGS. 1A, 1B). The reason has not clearly been identified, but this is probably because acoustic waves generated from each vibration board reach the article but only partially reflect off the same to primarily absorb or scatter on the surface of the article, thereby allowing the pressing force of the acoustic radiation pressure to concentrate in the article's direction.

In fact, since the fine mist 31*a* is miniaturized by ultrasonic vibration to have smaller particle sizes and larger surface areas, it is believed that the evaporation efficiency of mists is high, resulting in repeated evaporation and condensation. The fine mist 31*a* is a highly-miniaturized mist to concentrate on external surfaces of the article 50 and form a uniform and thin condensed film on the external surfaces of the article 50. Therefore, no excessive condensation occurs on internal wall surfaces of the pass box 10.

Thus, the fine mist 31*a* of hydrogen peroxide is subjected to constant ultrasonic vibration to concentrate on the periphery of the article 50 with repeated evaporation, condensation, and miniaturization. Even on the external surfaces of the article 50, the fine mist 31*a* is subjected to constant ultrasonic vibration to cause repeated re-evaporation and condensation of a uniform and thin condensed film. Accordingly, it is believed that ultrafine particles of hydrogen peroxide 3 μm or less and a hydrogen peroxide gas are subjected to phase change for coexistence on the periphery of the article 50 to provide high-level decontamination environment.

Also, by repeated re-evaporation and condensation of the uniformly and thinly formed condensed film on the external surfaces of the article 50, the concentration of a decontamination agent in a decontamination mist can be increased and efficient decontamination can be performed with a small amount of decontamination agent. Such an efficient decontamination with a small amount of decontamination agent can improve the efficiency of aeration after decontamination and reduce the duration of decontamination operations. Furthermore, the secondary effect is that ultrasonic vibration and acoustic radiation pressure by the sound flows 41*b*, 42*b*, 43*b*, 44*b* can remove a deposit on the external surfaces of the article 50 and the internal wall surfaces of the isolator 10.

Subsequently, the action of decontamination of the pass box 10 including the decontamination device 20 according to this first embodiment will be described by reference to examples. The present invention is not restricted to the following examples.

EXAMPLE

Figure 3:
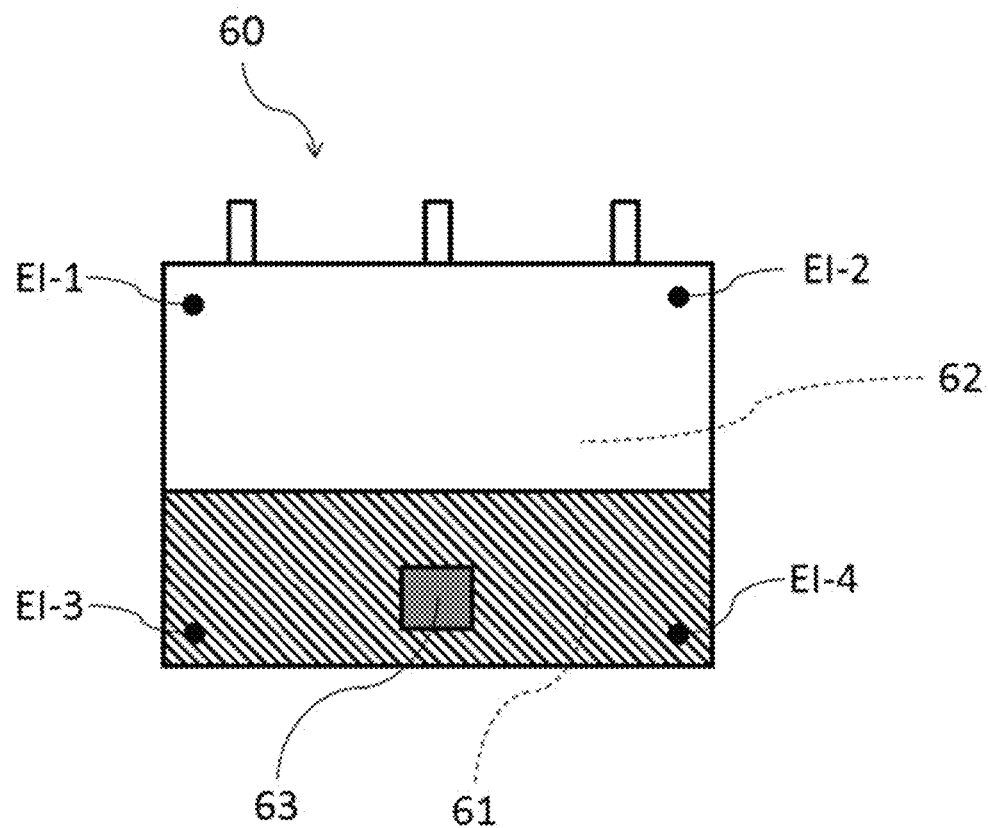
FIG. 3 is a schematic front view showing a medical infusion bag used in examples.

In this example, operations of decontaminating external surfaces of a medical infusion bag in a pass box and conveying it to the inside of an isolator was performed. FIG. 3 is a schematic front view showing a medical infusion bag used in this Example. In FIG. 3, a medical infusion bag 60 is a pouch made of polyethylene sized 20 cm in length, 24 cm in width and 0.2 cm in thickness, and in this Example, a distilled water 61 and an air 62 were filled therein, in place of a chemical. A thermocouple 63 is provided on the surface of the medical infusion bag 60 in the center lower direction.

Decontamination effects on external surfaces of the medical infusion bag 60 were confirmed by an enzyme indicator (EI). EI is an apparatus for fluorescence assay of residual enzymatic activity after a test to confirm decontamination effects, and this approach is advantageous in removing culture operations in conventional biological indicator (BI) and reducing the duration of operations. EI's comparative equality with BI was recently confirmed and the EI technique has proactively been used. The log spore reduction (LRD) value was calculated by the logarithmic decrement of fungi from the EI's fluorescence intensity after decontamination, and the LRD of 4 to 6 or more was judged as a sufficiently acceptable decontamination standard effect inside the pass box. EI-1 to EI-4 were disposed at 4 portions on external surfaces of the medical infusion bag 60 (see FIG. 3).

Figures 4A, 4B:
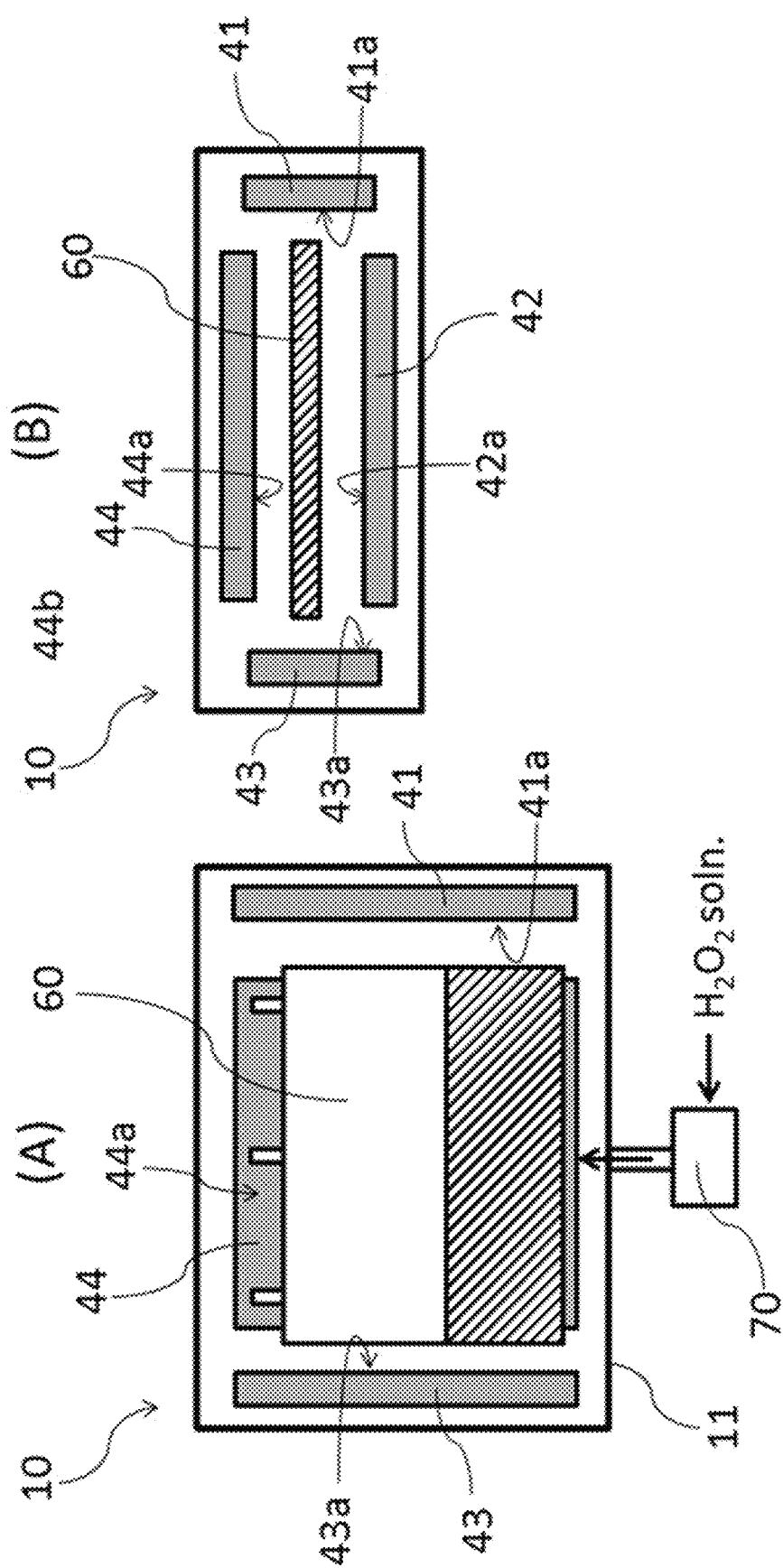
FIG. 4A is a schematic front cross-sectional view and FIG. 4B is a schematic plane cross-sectional view, each showing the inside of a pass box used in examples.

In this Example, a small pass box more preferably corresponding to the medical infusion bag 60 than the pass box in FIGS. 1A, 1B was used. FIG. 4A is a schematic s-sectional view and FIG. 4B is a schematic lane cross-sectional view, each showing the inside of a pass box used in this Example. A pass box 10 disposed is 0.012 m$^3$ in volume (30 cm in length, 35 cm in width, 12 cm in thickness; and internal wall surfaces are stainless plates), including 4 vibration boards 41, 42, 43, 44. The mist supply unit for converting hydrogen peroxide (35 W/V %) into a mist used is an ultrasonic humidifier 70 (nebulizer) in place of a two-fluid spray nozzle. The configuration of other portions is the same as the above first embodiment.

The input of a hydrogen peroxide solution into a pass box 110 was determined by 2 standards: 1.8 g (decontaminated at an input speed of 0.6 g/min for 3 minutes) and 5.5 g (decontaminated at an input speed of 5.5 g/min for one minute). Also, with an air input of 50 L/3 min as a post-decontamination aeration condition, each vibration board was operated. A test was performed by defining the case where 4 vibration boards disposed in a pass box are operated for each input of a hydrogen peroxide solution as Example, and the case where the 4 vibration boards are not operated as Comparative Example. The initial temperature of the medical infusion bag 60 was normal temperature. Table 1 shows the LRD values of EI-1 to EI-4 of Example and Comparative Example after decontamination operation.

TABLE 1

| Hydrogen peroxide | | | | | | | | Temperature rise |
|---|---|---|---|---|---|---|---|---|
| Speed (g/min) | Time (min) | Total amount (g) | | EI-1 | EI-2 | EI-3 | EI-4 | ($\Delta$T) |
| 0.6 | 3 | 1.8 | Embodiments | 8.7 | 8.8 | 7.6 | >9.0 | +1.0° C. |
|  |  |  | Comparative Example | <2.5 | <2.5 | 7.5 | 6.8 | +0.1° C. |
| 5.5 | 1 | 5.5 | Embodiments | 7.7 | 7.3 | >9.0 | >9.0 | +1.0° C. |
|  |  |  | Comparative Example | 8.2 | 6.9 | >9.0 | >9.0 | +0.1° C. |

As shown in Table 1, in cases where the input of a hydrogen peroxide solution is small (1.8 g), the LDR values in the pass box by operating the 4 vibration boards are found to provide sufficient effects at any position, resulting in uniform decontamination. In contrast, the LRD values in Comparative Example show many insufficiently decontaminated areas at the upper portion of the medical infusion bag, which fail to reach the value of 4LRD. On the other hand, in any case where the input of the hydrogen peroxide solution is large (5.5 g), sufficient decontamination effects were confirmed, regardless of whether the 4 vibration boards are operated or halted. It is thus found that using the decontamination device according to this embodiment 1, the supply of a hydrogen peroxide solution even in small quantities can obtain sufficient decontamination effects.

Therefore, according to this first embodiment, the present invention can provide a decontamination device capable of accomplishing a decontamination effect with a proper amount of decontamination agent by employing a mist control mechanism and concentrating a mist for decontamination on the surface of an article to be conveyed, and reducing the duration of operations such as aeration to achieve more efficient decontamination works, and a pass box in which same is disposed.

Second Embodiment

Figures 5A, 5B:
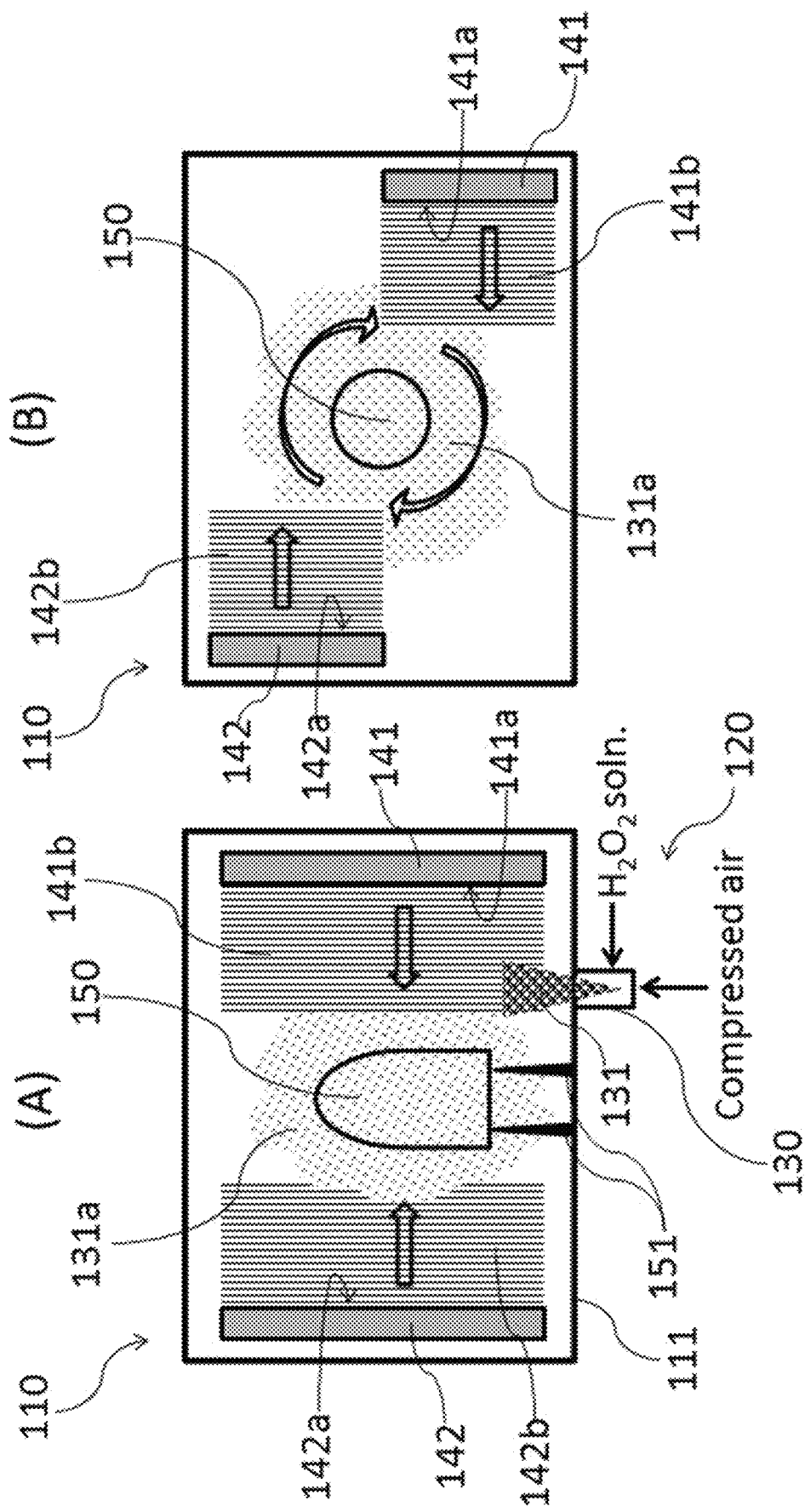
FIG. 5A is a schematic front cross-sectional view and FIG. 5B is a schematic plane cross-sectional view, each showing the inside of a pass box including a decontamination device according to a second embodiment.

While the above first embodiment relates to a decontamination device including 4 vibration boards that are opposite each other, this second embodiment relates to a decontamination device placed in a pass box including 2 vibration boards that are not opposite each other, which will be described. FIG. 5(A) is a schematic front cross-sectional view and FIG. 5(B) is a schematic plane cross-sectional view, each showing the inside of a pass box including the decontamination device according to the second embodiment.

In FIGS. 5A, 5B, a pass box 110 is a stainless housing that is linked to an isolator (not shown) through an opening/closing door (inner door) on a wall surface thereof, the isolator including an opening/closing door (outer door) on other wall surface, leading to the external environment. The linking state between the pass box 110 and the isolator and the structure of opening/closing doors are not particularly restricted, and the pass box is the same as conventional pass boxes in structure. The position of the pass box relative to the isolator is not restricted to that on a side wall surface, and the pass box may be linked to a top wall surface or a bottom wall surface. The inside of the pass box may include an air supply and exhaust device for decontamination and aeration. FIG. 5 shows no inner door, outer door, air supply and exhaust device, or the like.

In FIGS. 5A, 5B, an article 150 that is conveyed from the external environment to the inside of the isolator is conveyed to a center inside the pass box 110. In this second embodiment, the article 150 is to be decontaminated and is conveyed to the inside of the isolator after it is decontaminated by a decontamination device 120 in the pass box. In FIG. 5A, the article 150 is supported by a deck 151 such that its bottom surface is readily decontaminated.

In FIGS. 5A, 5B, the pass box 110 includes therein a decontamination device 120. The decontamination device 120 is composed of a mist supply device 130, a mist control unit 140, and an ultrasonic controller (not shown). In this second embodiment, the mist supply unit used 130 is a two-fluid spray nozzle 130 placed on a bottom wall surface 111 of the pass box 110 (see FIG. 5A). In this second embodiment, the decontamination device used is a hydrogen peroxide solution ($H_2O_2$ solution).

The two-fluid spray nozzle 130 converts a hydrogen peroxide solution into a hydrogen peroxide solution mist 131 by compressed air from a compressor (not shown) to supply the same to the inside of the pass box 110. In the present invention, the mist supply unit is not restricted to a two-fluid spray nozzle, and a mist generation mechanism and output are not particularly restricted.

Herein, a mist control unit 140 will be described. In this second embodiment, the mist control unit 140 includes 2 vibration boards 141, 142. The 2 vibration boards 141, 142 are disposed inside the pass box 110 against side wall surfaces at 2 portions: a right wall surface lower portion and a left wall surface upper portion shown in FIG. 5B such that vibration surfaces 141a, 142a face horizontally inside the pass box 110. These 2 vibration boards 141, 142 are arranged without allowing board surfaces (vibration surfaces) thereof to be opposite each other. The reason for arranging the 2 vibration boards 141, 142 without being opposite each other and the action of the hydrogen peroxide solution mist 131 will be described later.

Herein, the vibration boards 141, 142 will be described. These vibration boards 141, 142 are the same as the vibration boards 41, 42, 43, 44 in the above first embodiment in structure (see FIG. 2). The frequency and output of these vibration boards 141, 142 are also the same as those of the vibration boards in the above first embodiment.

Subsequently, the action of the hydrogen peroxide solution mist 131 inside the pass box 110 including the decontamination device 120 according to the above configuration will be described. In FIG. 5B, the vibration board 141 disposed at the right lower portion shown inside the pass box 110 allows the vibration surface 141a thereof to face in the left direction shown.

Ultrasonic vibration of the ultrasonic speaker 46 in this state allows a significantly directional sound flow 141b traveling in the air in the vertical direction (in the left direction shown in FIG. 5B) from the vibration surface 141a to take in a hydrogen peroxide solution mist 131 discharged from the two-fluid spray nozzle 130, generate a pressing force by acoustic radiation pressure and move the same in the direction of the sound flow 141b (in the left direction shown in FIG. 5B). In this case, the hydrogen peroxide solution mist 131 is converted into a fine mist 131a miniaturized by ultrasonic vibration from the sound flow 141b and circulate so as to rotate inside the pass box 110.

Meanwhile, the vibration board 142 disposed at the left upper portion in FIG. 5B inside the pass box 110 allows the vibration surface 142a thereof to face in the right upper direction shown. Ultrasonic vibration of the ultrasonic speaker 46 in this state allows a significantly directional sound flow 142b traveling in the vertical direction (in the right direction shown in FIG. 5B) from the vibration surface 142a to generate a pressing force from acoustic radiation pressure on the fine mist 131a miniaturized and sent by the sound flow 141b and to move the same in the direction of the sound flow 142b (in the right direction shown in FIG. 5B). In this case, the hydrogen peroxide solution mist 131a is converted into a fine mist that is more stabilized by ultrasonic vibration from the sound flow 142b and circulate so as to rotate inside the pass box 110.

Thus, the fine mist 131a miniaturized and stabilized by the sound flows 141b and 142b circulate so as to rotate in the curved arrow direction shown in FIG. 5B (clockwise) inside the pass box 110. Inventors of the present invention found that in this state the fine mist 131a miniaturized by ultrasonic vibration from the sound flows 141b 142b circulates to rotate by concentrating around the external surfaces of the article 50 located at the central portion of the pass box 10 (see FIG. 5B). The reason has not clearly been identified, but this is probably because acoustic waves generated from each vibration board reach the article to diffract primarily along a side surface of the article from each vibration board.

Also, since the fine mist 131a is miniaturized and then has a small particle size and a large area surface, the evaporation efficiency of mists is high, resulting in uniform humidification and decontamination of external surfaces of the article 150. Therefore, no excessive condensation occurs on internal wall surfaces of the pass box 110 since the fine mist 131a concentrates on external surfaces of the article 150.

Accordingly, the concentration of a decontamination mist can be increased and efficient decontamination can be performed with a small amount of decontamination agent. Such an efficient decontamination with a small amount of decontamination agent can improve the efficiency of aeration after decontamination and reduce the duration of decontamination operations. Furthermore, the secondary effect is that ultrasonic vibration and acoustic radiation pressure by the sound flows 141b, 142 can remove a deposit on internal wall surfaces of the pass box 110.

Therefore, according to this second embodiment, the present invention can provide a decontamination device capable of accomplishing a decontamination effect with a proper amount of decontamination agent by employing a mist control mechanism and concentrating a mist for decontamination on the surface of an article to be conveyed, and reducing the duration of operations such as aeration to achieve more efficient decontamination works, and a pass box in which same is disposed.

The goal of the present invention is achieved by not only each of the above embodiments, but also by the following various alternatives.
  (1) In each of the above embodiments, a pass box is illustrated as a room to be decontaminated. However, the room to be decontaminated is not restricted thereto, and internal and local decontamination may be performed inside an isolator, LABS, or the like. Also, a mist supply unit or a mist control unit (vibration board) of a decontamination device may be fixed in a working chamber, or may be introduced only for decontamination.
  (2) In each of the above embodiments, a mist supply unit used is a two-fluid spray nozzle. However, the mist supply unit is not restricted thereto, and an ultrasonic humidifier (nebulizer) used in the example or a single-fluid spray nozzle may be used. Also, a combination of a plurality of mist supply units may be used.

(3) In each of the above embodiments, a vibration board of a mist control unit used includes a plurality of ultrasonic speakers placed in a speaker base. However, the vibration board is not restricted thereto, and any type of vibration board may be used so long as it includes a Langevin type transducer fixed to a stainless steel having a constant area or a board surface for ultrasonic vibration.

(4) In each of the above embodiments, a vibration board of a mist circulation dispersion unit used includes a plurality of ultrasonic speakers placed in a speaker base such that the ultrasonic speakers are uniform in transmission direction and these ultrasonic speakers are operated in the same phase. However, the vibration board of a mist circulation dispersion unit is not restricted thereto, and a plurality of ultrasonic speakers may be operated in a different phase.

(5) In each of the above embodiments, a decontamination agent used is a hydrogen peroxide solution ($H_2O_2$ solution). However, the decontamination agent is not restricted thereto, and it may be any type of decontamination agent so long as it is liquid.

(6) In the above first embodiment, 4 vibration boards are arranged on 4 side walls. However, the configuration is not restricted thereto, and vibration boards may be arranged on 2 to 6 vibration boards out of 6 boards including a top wall surface and a bottom wall surface.

(7) In the above first embodiment, 2 vibration boards are arranged so as to be opposite each other. However, the positional relationship is not restricted thereto, and ultrasonic reflection boards may be arranged so as to be opposite each other relative to one vibration board.

(8) In the above second embodiment, the circulating direction of a decontamination agent mist is horizontal direction in cases where 2 vibration boards are arranged on 2 side walls so as not to be opposite each other. However, the circulation direction is not restricted thereto, and the circulating direction of a decontamination agent mist may be vertical direction in cases where 2 vibration boards may be arranged on a top wall and a bottom wall so as not to opposite each other.

(9) In the above second embodiment, the circulating direction of a decontamination agent mist is horizontal direction in cases where 2 vibration boards are arranged on 2 side walls so as not to be opposite each other. However, the circulation direction is not restricted thereto, and the circulating direction of a decontamination agent mist may be vertical direction in cases where 4 vibration boards may be arranged on 4 side walls so as not to opposite each other.

REFERENCE SIGNS LIST 10, 110 . . . Pass box, 11, 111 . . . Bottom wall surface,
20, 120 . . . Decontamination device,
30, 130 . . . Mist supply means (Two-fluid spray nozzle),
31, 131 . . . Hydrogen peroxide solution mist, 31a, 131a . . . Fine mist,
40, 140 . . . Mist control mechanism,
41, 42, 43, 44, 141, 142 . . . Vibration board,
41a, 42a, 43a, 44a, 141a, 142a . . . Vibration surface,
41b, 42b, 43b, 44b, 141b, 142b . . . Sound flow,
45 . . . Speaker base, 45a . . . Plane or planar surface of speaker base,
46 . . . Ultrasonic speaker, 46a . . . Vibrating surface of ultrasonic speaker,
50, 150 . . . Article, 51, 151 . . . Deck,
60 . . . Medical infusion bag, 61 . . . Distilled water, 62 . . . Air,
63 . . . Thermocouple,
70 . . . Ultrasonic humidifier (Nebulizer),
EI-1 to EI-4 . . . Enzyme indicator.

The invention claimed is:

1. A decontamination device for decontaminating an article accommodated inside a working chamber of a pass box, comprising:
a mist supply means and a mist control mechanism, wherein
the mist supply means is configured to convert a chemical for decontamination provided thereto into a mist for decontamination, and to supply the mist to the inside of the working chamber dimensioned to accommodate the article,
the mist control mechanism includes vibration boards disposed adjacent to internal wall surfaces of the working chamber,
wherein the vibration boards are configured to generate sound flows with ultrasonically vibrating transmitters located at the vibration boards, said sound flows directed from board surfaces by an ultrasound in a vertical direction to press the mist for decontamination supplied to the inside of the working chamber by a resulting pressing force caused by acoustic radiation to concentrate the mist for decontamination on external surfaces of the article.

2. The decontamination device according to claim 1, wherein the mist control mechanism comprises a plurality of vibration boards,
the plurality of vibration boards is arranged with the article placed therebetween,
wherein the board surfaces of the vibrational boards are disposed opposite each other such that the resulting pressing force is primarily directed in a direction of the article from each of the vibration boards, and
the mist for decontamination is controlled to concentrate on external surfaces of the article.

3. The decontamination device according to claim 1, wherein
the mist control mechanism includes a plurality of vibration boards, the plurality of vibration boards is arranged with the article placed therebetween and without board surfaces thereof being opposite each other such that the resulting pressing force is primarily directed along a side surface of the article from each of the vibration boards, and the mist for decontamination is controlled to concentrate on external surfaces of the article by moving so as to rotate inside the working chamber.

4. The decontamination device according to claim 3, wherein
a vibration board of the plurality of vibration boards includes a base and a plurality of transmitters,
transmitters from the plurality of transmitters are spatially uniformly arranged on a plain planar surface of the base so as to be uniform in transmission direction, and the transmitters are operated in the same phase with one another, whereby
a sound flow is generated by a significantly directional ultrasound from the board surface of the vibration board in the vertical direction by mutually amplifying ultrasound outputs from the plurality of transmitters in a front direction and mutually canceling out the ultrasound outputs of the plurality of transmitters in a lateral direction.

5. The decontamination device according to claim 4, configured to miniaturize
the mist for decontamination supplied to the inside of the working chamber is further miniaturized by ultrasonic vibration generated from the vibration board.

6. The decontamination device according to claim 5, wherein
the decontamination device comprises a control means configured to change frequency and output of the ultrasound generated from the vibration board and/or to transmit for said ultrasound intermittently to control a position or moving speed of the mist for decontamination controlled to concentrate on external surfaces of the article.

7. A pass box wherein the decontamination device according to claim 6 is disposed.

8. The decontamination device according to claim 2, wherein
a vibration board of the plurality of vibration boards includes a base and a plurality of transmitters,
the plurality of transmitters is arranged on a planar surface of the base spatially uniformly, and transmitters from said plurality are operated in the same phase with one another, whereby
a sound flow is generated by a significantly directional ultrasound from the board surface of the vibration board in the vertical direction by mutually amplifying ultrasound outputs from the plurality of transmitters in a front direction and mutually canceling out the ultrasound outputs of the plurality of transmitters in a lateral direction.

9. The decontamination device according to claim 8, configured to miniaturize the mist for decontamination supplied to the inside of the working chamber by ultrasonic vibration generated from the vibration board.

10. The decontamination device according to claim 9, wherein
the decontamination device comprises a control means configured to change frequency and output of the ultrasound generated from the vibration board and/or to transmit said ultrasound intermittently to control a position or moving speed of the mist for decontamination controlled to concentrate on external surfaces of the article.

11. A pass box wherein the decontamination device according to claim 10 is disposed.

* * * * *